United States Patent [19]
Dietrich

[11] 4,059,013
[45] Nov. 22, 1977

[54] LABORATORY TEST DEVICE FOR TEXTILE SAMPLES

[75] Inventor: Roland Dietrich, Liestal, Switzerland
[73] Assignee: Ahiba AG, Switzerland
[21] Appl. No.: 720,477
[22] Filed: Sept. 3, 1976
[30] Foreign Application Priority Data
 Sept. 5, 1975 Switzerland ............ 11512/75
[51] Int. Cl.² .................. B01F 8/10; D06B 5/22
[52] U.S. Cl. .......................... 73/159; 68/171;
 73/150 R; 366/147; 366/233
[58] Field of Search ............ 73/159, 61.1 R; 259/57,
 259/58, DIG. 18; 68/147, 171

[56] References Cited
 U.S. PATENT DOCUMENTS

| 2,660,055 | 11/1953 | Thommen | 73/159 |
| 2,749,740 | 6/1956 | Stiegler | 73/159 X |
| 2,810,836 | 10/1957 | Hutgens | 73/159 X |
| 2,862,383 | 12/1958 | Stiegler | 73/159 X |

FOREIGN PATENT DOCUMENTS 1,061,285  3/1967  United Kingdom ........ 73/159

Primary Examiner—Daniel M. Yasich
Attorney, Agent, or Firm—Ladas, Parry, Von Gehr, Goldsmith & Deschamps

[57] ABSTRACT

The invention concerns an improved device for testing textile samples in the laboratory. The device includes a tank holding a heating liquid. Test containers attached to test container holders are placed in the tank and containers and holders rotated. Rotation is achieved by transmitting the drive from rolls positioned on drive shafts to drive wheels forming an integral part of the container holders.

2 Claims, 1 Drawing Figure

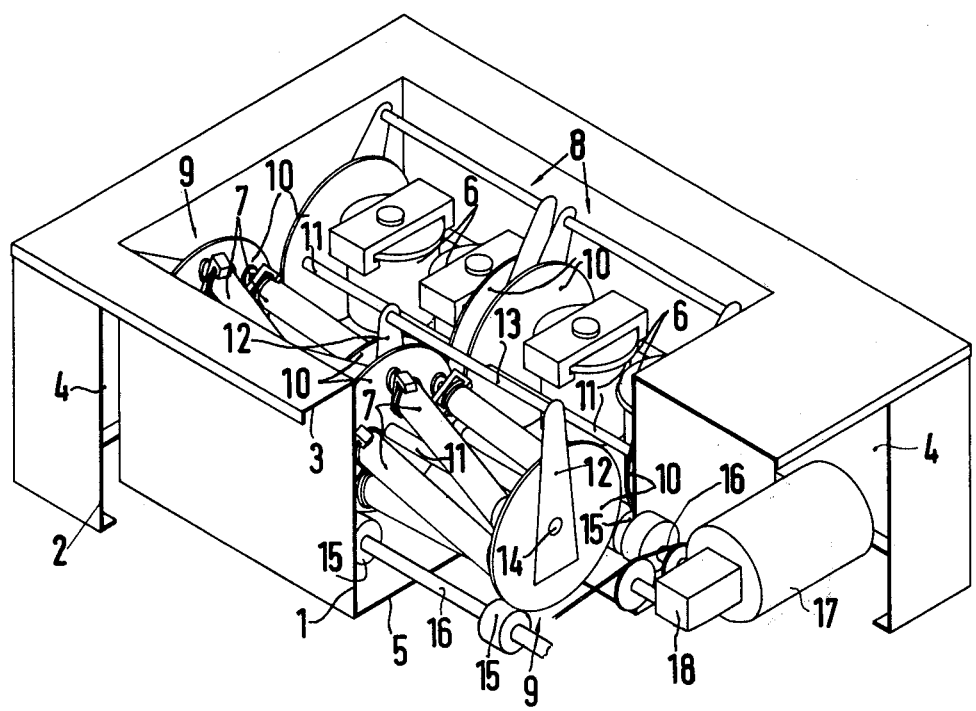

LABORATORY TEST DEVICE FOR TEXTILE SAMPLES

The present invention relates to a laboratory test device for textile samples, in particular to a device for carrying out fastness tests and dyeing tests.

In order to obtain reliable data on the wear properties of textiles, made of fibres of all kinds, for clothes, household linen, industrial purposes etc., it is very important to be able to carry out reproducible tests under exactly defined conditions. In the testing of textiles to determine their suitability for these various uses, their behaviour when being dyed and laundered is of particular importance. A number of laboratory test devices have therefore been marketed for testing the fastness of dyeings and the effect of various detergents on the fibres. Most of these devices are intricate in their design, above all in that of the drive mechanism for the continuous or discontinuous movement of the sample containers. The design of the sample containers themselves is usually also complex, making these devices difficult to use.

The object of the present invention is therefore to propose a laboratory test device for textile samples, having a simple, easily understandable design and containers which can be removed and replaced conveniently and without difficulty.

The laboratory test device of the invention has a tank for accommodating a heating liquid and a plurality of test containers movably disposed in this liquid and is characterized in that the test containers are attached in groups to a support member which includes two parallel, coaxial drive wheels of the same diameter positioned a certain distance appart and means for rigidly linking the two drive wheels to each other, further characterized in that drive means for said support member are located in the tank, said drive means having horizontal, mutually parallel shafts which work in pairs and which have parts the peripheries of which rotate at the same speed and the surfaces of which engage the peripheries of the drive wheels.

An illustrative embodiment of the device of the invention is described below with reference to the Drawing which shows a perspective, partly cut-away view of the device.

In the Drawing, reference numberal 1 denotes a tank which can contain a heating liquid. The tank is surrounded by a casing 2, the upper edge of which is joined to the horizontal rim 3 of the tank 1. The space 4 between the side walls of the tank and the casing 2 can be used to accommodate both insulating material and the motor 17 and gearbox 18 for the drive system for the device as shown on the right-hand side of the Drawing. Depending whether the device is designed as a built-in or bench-top model and depending how the space 4 is to be used, the lower edge of the casing 2 can be free-standing as shown or connected with the floor 5 of the tank.

The tank 1 is designed to accommodate a number of test containers 6 and/or 7 and their associated holders 8 and/or 9. The design of the test containers themselves is unimportant to the invention and only the container holders and the way they are driven is described below. The container holders 8, 9 are disposed next to each other in parallel rows in the tank, the Drawing showing two rows, each of two container holders.

Each of the container holders 8, 9 includes two circular drive wheels 10 which are located one at each end of the container holder, have the same diameter and are rigidly connected to each other by spacer means, such as bolts 11 or equivalent means. Each container holder further includes carrying means consisting of a pair of side plates 12 (only indicated for one of the container holders) and a handle 13 connecting the two side plates. The side plates 12 are situated on the outer sides of the drive wheels 10 and are pivotally mounted on central bearings 14. The two drive wheels 10, 10 and the connecting bolts 11 or equivalent means of each of the container holders 8, 9 thus form a support member which holds the test containers, the support members being freely rotatable with respect to the carrying means by virtue of the bearing 14. The carrying means 12, 13 enable the container holders to be introduced into and removed from the tank without any difficulty.

When the container holders 8, 9 are in the tank 1, their support members make contact with drive means which include, for each row of container carriers, a pair of drive shafts 16 provided with roll bodies 15. The drive shafts 16 are rotatably mounted in bearings (not shown) near the bottom 5 of the tank. The roll bodies are of such a width and are so positioned on the shafts 16 that they support the drive wheels 10 when the container holders are in position in the tank. Their diameter is preferably 1.5 to 4 times that of the shaft. The drive shafts 16 are coupled to each other either inside or outside the tank 1 and are rotated by a motor 17 and gearbox 18 situated outside the tank. The support members holding the test containers 6, 7 are in turn rotated by the drive wheels 10 resting against the roll bodies 15, while the carrying means 12, 13 remains stationary in a stand-by position.

The test containers may be joined to the support member by any conventional fastening means located on the support member. They execute a continuous tumbling or rotating motion about the axis of rotation of the support member when the device is in operation. The liquour in the test containers is thereby constantly agitated and the test specimens constantly shaken from the bottom to the top of the test containers. The test containers are closed in the usual way with screw, bayonet or clip closures so that the liquid cannot leak out of the containers and the heating fluid cannot penetrate into them.

Devices of the type described above are suitable for carrying out fastness tests on textile samples, e.g. wash-fastness tests to determine the resistance of the fabric at particular temperatures to the conditions experienced during laundering, dry-cleaning fastness tests and fulling fastness tests. The device is however also suitable for use as a laboratory dyeing apparatus.

The device may be operated open at the top (as in the Drawing) or with a hinged cover. A suitable heating fluid may be used to give temperatures of up to 140° C.

What we claim is:

1. In a laboratory test device for textile samples in a testing liquid of the type for carrying out reproducible fastness tests and dyeing tests, having a tank for accommodating a heating liquid and a plurality of liquid impermeable test containers for holding the textile samples, said containers are detachably secured to at least one support member and are movably disposed in the heating liquid whereby the test containers are continuously tumbled within the heating liquid, wherein the improvement comprises the test containers being attached in groups to the support member which includes two parallel, coaxial drive wheels of the same diameter positioned a certain distance apart and means for rigidly linking the two drive wheels to each other, driving means cooperating with said support member being located in the tank, said driving means including at least one pair of horizontal, parallel shafts which are simultaneously driven to rotate at the same speed and which have a plurality of roll bodies disposed thereon, the peripheries of which rotate at the same speed, and the outer surfaces of said roll bodies being positioned on said at least one pair of shafts to engage the perpheries of said drive wheels.

2. A device according to claim 1, characterized by the fact that said roll bodies have portions that are substantially cylindrical and have a diameter 1.5 to 4 times that of said parallel shafts.

* * * * *